United States Patent [19]

Hasunuma et al.

[11] 4,000,276

[45] Dec. 28, 1976

[54] COSMETIC COMPOSITION CONTAINING VITAMIN E OROTATE

[75] Inventors: Kyotaro Hasunuma; Takashi Abe; Masahiro Kurokawa, all of Odawara, Japan

[73] Assignee: Kanebo, Ltd., Tokyo, Japan

[22] Filed: Sept. 24, 1973

[21] Appl. No.: 399,846

[30] Foreign Application Priority Data

Sept. 29, 1974 Japan .......................... 47-98323

[52] U.S. Cl. .......................... 424/251; 424/70; 424/168; 424/170; 424/365
[51] Int. Cl.² .......................... A61K 31/505
[58] Field of Search .......................... 424/284, 251, 365; 260/345.5

[56] References Cited

UNITED STATES PATENTS

| 2,723,278 | 11/1955 | Surmatis | 260/345.5 |
| 3,803,179 | 4/1974 | Ahrens | 260/345.5 |
| 3,825,563 | 7/1974 | Ahrens | 260/345.5 |

FOREIGN PATENTS OR APPLICATIONS 2,144,249 3/1972 Germany .......................... 424/284

OTHER PUBLICATIONS

Chemical Abstracts 1964, vol. 60, pp. 8001–8002.

*Primary Examiner*—Dale R. Ore
*Attorney, Agent, or Firm*—Kenyon & Kenyon

[57] ABSTRACT

Cosmetics containing vitamin E orotate and having a very refreshing effect on human skin.

6 Claims, No Drawings

COSMETIC COMPOSITION CONTAINING VITAMIN E OROTATE

The present invention relates to improved cosmetics, particularly cosmetics effective for refreshing human skin. It is known that vitamin E has an influence on the human sexual organs, and, therefore, is effective for healing woman skin diseases which have been caused by menstrual irregularity and menopause.

Further, it is known that vitamin E is effective for curing chilblain, exudative erythema and frostbite, due to its vasodilative action. However, vitamin E is not or only negligibly, effective for moisturizing and beautification of the skin including fining the texture of skin. Further, when utilized in cosmetics, vitamin E has the disadvantages that the vitamin E is readily decomposed by action of heat or light or during a long period of storage, which results in discoloration and emission of a bad smell. The bad smell of the decomposed vitamin E cannot be removed by addition of perfume.

Orotic acid (1,2,3,6-tetrahydro-2,6-dioxo-4-pyrimidine-carboxylic acid; uracil-6-carboxylic acid) which may be prepared by the condensation of urea and monoethyl ester of oxalacetic acid in methyl alcohol, has a high stimulation effect for the multiplication of lactobacillus bulgaris. Orotic acid is also effective for promoting the growth of rats. Recently, it was reported that orotic acid has a moisturizing effect for human skin similar to that of pyrrolidone carboxylic acid. However, orotic acid is difficult to utilize in cosmetics because of its negligible solubility in water and organic solvents. On the other hand, the alkali metal salts of orotic acid are soluble in water. However, when such orotic salts are utilized in cosmetics the orotic salts merely have a temporary effect, because the orotic salts cannot be maintained in skin tissue for a long time. Therefore, the alkali metal salts or orotic acid cannot be expected to be a valuable additive of cosmetics effective for the beautification of human skin.

Also, it is known that acetic ester of vitamin E tends to be easily hydrolyzed, and the hydrolyzed compound gives out a bad odor of acetic acid. Further, the acetic ester of vitamin E has a relatively low beautification effect on human skin.

The inventors have systematically studied a wide range of cosmetic additives to eliminate the above-mentioned disadvantages of the conventional cosmetic additives, and discovered the fact that an orotic ester of vitamin E (vitamin E orotate) has a very excellent capability of beautifying human skin and that such capability cannot be expected from the properties of either the orotic acid or vitamin E. That is, the vitamin E orotate when contained in cosmetics is highly effective for moisturizing the skin and fining its texture, so as to beautify the human skin by stimulating the skin and cell functions. The present invention was accomplished based on the above-mentioned discovery.

The object of the present invention is to provide improved cosmetics having an excellent capability of beautifying human skin.

The above object of the present invention can be accomplished by providing cosmetics containing a vitamin E orotate.

The vitamin E orotate useful for the cosmetics of the present invention is a platy crystal having a melting point of 183° to 188° C, which may be prepared by esterifying vitamin E with orotyl chloride or orotic anhydride. The term "vitamin E" used herein refers to α-tocopherols which include dl-α-tocopherol, d-α-tocopherol and l-α-tocopherol, β-tocopherol, γ-tocopherol, δ-tocopherol and mixtures of two or more of the above-mentioned compounds. The cosmetics of the present invention may be in the form of skin cream, lotion, hair cream, nutritious skin oil and other conventional cosmetics and preferably contain 0.01 to 15%, more preferably, 0.05 to 10% of the vitamin E orotate based on the weight of the cosmetic. In the preparation of the cosmetics of the present invention, the vitamin E may be directly mixed with a cosmetic base, for example, oil base, emulsion base or cream base, or previously dissolved in an oily substance or alcoholic solvent and then emulsified, mixed, or dissolved in other base material.

The vitamin E orotate contained in the cosmetic base is absorbed and maintained by the human skin over a long period of time. The vitamin E orotate maintained in the human skin stimulates the skin function and activates the skin cells, which actions may also be promoted by other additives contained in the cosmetics. Accordingly, the cosmetics of the present invention containing the vitamin E orotate can beautify the human skin, that is, improve the texture, complexion and gloss of the skin, by stimulating the roots of hairs. Such remarkable effects of the vitamin E orotate enhance the commercial worth of the cosmetics of the present invention.

Various methods of practicing the present invention are illustrated by the following examples. These examples are intended merely to illustrate the present invention and not in any sense to limit the manner in which the present invention may be practiced.

EXAMPLE 1

Preparation of skin cream

An oil phase base containing 0.5 part by weight of vitamin E orotate was prepared by mixing the cosmetic components of the composition as shown in Table 1. Separately, an aqueous phase base was prepared by dissolving the components of the composition as shown in Table 1 in distilled water. Then, the oil phase base was uniformly emulsified in the aqueous phase base by stirring at a temperature of 80° C, and the emulsion was gradually cooled to room temperature to form a cream of the present invention.

Table 1

| Base | Component | Composition (part by weight) | | | | |
|---|---|---|---|---|---|---|
| | | Example | Comparison Example | | | |
| | | 1 | 1 | 2 | 3 | 4 |
| | Bees wax | 3.0 | 3.0 | 3.0 | 3.0 | 3.0 |
| | Stearic acid | 8.0 | 8.0 | 8.0 | 8.0 | 8.0 |
| | Cetyl alcohol | 3.0 | 3.0 | 3.0 | 3.0 | 3.0 |
| | Anhydrous lanolin | 4.0 | 4.0 | 4.0 | 4.0 | 4.0 |
| | Olive oil | 4.0 | 4.0 | 4.0 | 4.0 | 4.0 |

Table 1-continued

|  |  | Composition (part by weight) | | | | |
|---|---|---|---|---|---|---|
|  |  | Example | Comparison Example | | | |
| Base | Component | 1 | 1 | 2 | 3 | 4 |
| Oil phase | Sorbitan monostearate | 2.0 | 2.0 | 2.0 | 2.0 | 2.0 |
|  | Addition product of sorbitan monopalmitate with polyoxyethylene | 3.0 | 3.0 | 3.0 | 3.0 | 3.0 |
|  | p-Hydroxyethyl benzoate | 0.1 | 0.1 | 0.1 | 0.1 | 0.1 |
|  | Perfume | 0.5 | 0.5 | 0.5 | 0.5 | 0.5 |
|  | Vitamin E orotate | 0.5 | — | — | — | — |
|  | Vitamin E | — | 0.5 | — | — | — |
|  | Vitamin E acetate | — | — | 0.5 | — | — |
|  | Orotic acid | — | — | — | 0.5 | — |
| Aqueous phase | Propylene glycol | 5.0 | 5.0 | 5.0 | 5.0 | 5.0 |
|  | Glycerol | 3.0 | 3.0 | 3.0 | 3.0 | 3.0 |
|  | Borax | 0.2 | 0.2 | 0.2 | 0.2 | 0.2 |
|  | Distilled water | 63.7 | 63.7 | 63.7 | 63.7 | 64.2 |

Four comparative creams were prepared by the same method as stated above using, instead of the vitamin E orotate, vitamin E (Comparison Example 1), vitamin E acetate (Comparison Example 2), orotic acid (Comparison Example 3) and nothing (Comparison Example 4).

In order to test the cosmetic actions of the creams prepared above, each cream was applied onto the faces of 20 women, between 25 and 45 years of age who suffered from facial wrinkles, twice a day (in the morning and evening) for a period of 6 months in succession. Based on the results of the tests, the cosmetic actions of the creams were evaluated as illustrated in Table 2. In Table 2, the numerals indicate the number of women evaluating the respective creams as having the described degree of effectiveness of the result indicated.

Table 2

| Result | Degree of effectiveness | Evaluation | | | | |
|---|---|---|---|---|---|---|
|  |  | Example | Comparison Example | | | |
|  |  | 1 | 1 | 2 | 3 | 4 |
| Fining effect for texture | Very effective | 18 | 0 | 0 | 0 | 0 |
|  | Noticeably effective | 1 | 10 | 11 | 7 | 1 |
|  | Slightly effective | 1 | 10 | 9 | 13 | 19 |
|  | No effect | 0 | 0 | 0 | 0 | 0 |
| Moisturizing effect for skin | Very effective | 18 | 0 | 0 | 0 | 0 |
|  | Noticeably effective | 1 | 0 | 0 | 0 | 0 |
|  | Slightly effective | 1 | 5 | 7 | 3 | 10 |
|  | No effect | 0 | 15 | 13 | 17 | 10 |
| Improving effect for complexion and gloss | Very effective | 17 | 0 | 0 | 0 | 0 |
|  | Noticeably effective | 1 | 0 | 0 | 0 | 0 |
|  | Slightly effective | 1 | 15 | 12 | 12 | 1 |
|  | No Effect | 1 | 5 | 8 | 8 | 19 |

As Table 2 definitely illustrates, the cream of the present example, containing the vitamin E orotate, is very effective for fining skin texture, moisturizing the skin and improving the complexion and the gloss of the skin, in comparison with the comparative creams of Comparison Examples 1 through 4. Particularly, it should be noted that Table 2 shows that the vitamin E orotate is much more effective for enhancing the cosmetic effects of the skin cream than the skin cream containing the vitamin E acetate. This is, the replacement of the orotic acid group for the acetic acid group of the vitamin E acetate results in an exceptionally effective capability of refreshing the women's skin.

EXAMPLE 2

Preparation of skin lotion

Referring to Table 3, an alcoholic base was prepared by dissolving vitamin E orotate in ethyl alcohol in the composition as shown in Table 3. Separately, an aqueous base was prepared by successively dissolving glycerol, propylene glycol, an addition product of hydrogenated castor oil with polyoxyethylene, sorbitol and perfume in distilled water in the composition as shown in Table 3. The aqueous base was added dropwise and uniformly mixed with the alcoholic base while stirring to prepare a skin lotion.

Four comparative skin lotions were prepared by the same procedures as mentioned above using instead of the vitamin E orotate, vitamin E (Comparison Example 5), vitamin E acetate (Comparison Example 6), orotic acid (Comparison Example 7) and nothing (Comparison Example 8).

Table 3

| Component | Example 2 | Comparison Example 5 | Comparison Example 6 | Comparison Example 7 | Comparison Example 8 |
|---|---|---|---|---|---|
| | Composition (part by weight) | | | | |
| Ethyl alcohol (95%) | 13 | 13 | 13 | 13 | 13 |
| Glycerol | 2 | 2 | 2 | 2 | 2 |
| Propylene glycol | 2 | 2 | 2 | 2 | 2 |
| Addition product of hydrogenated castor oil with polyoxyethylene | 1 | 1 | 1 | 1 | 1 |
| Sorbitol | 1 | 1 | 1 | 1 | 1 |
| Perfume | 0.5 | 0.5 | 0.5 | 0.5 | 0.5 |
| Vitamin E orotate | 0.05 | — | — | — | — |
| Vitamin E | — | 0.05 | — | — | — |
| Vitamin E acetate | — | — | 0.05 | — | — |
| Orotic acid | — | — | — | 0.05 | — |
| Distilled water | 80.45 | 80.45 | 80.45 | 80.45 | 80.50 |

In order to test the cosmetic actions of the skin lotions prepared above, each skin lotion was applied onto the skins of 20 women who suffered dry and rough skin, twice a day (in morning and evening) for a period of 3 months in succession.

Based on the results of the tests, the effects of the lotions for the dry and rough skins were evaluated as shown in Table 4.

Table 4

| Result | Degree of effectiveness | Example 2 | Comparison Example 5 | Comparison Example 6 | Comparison Example 7 | Comparison Example 8 |
|---|---|---|---|---|---|---|
| | | Evaluation | | | | |
| Moisturizing effect for skin | Very effective | 16 | 0 | 0 | 0 | 0 |
| | Noticeably effective | 2 | 0 | 0 | 0 | 0 |
| | Slightly effective | 2 | 7 | 9 | 6 | 5 |
| | No effect | 0 | 13 | 11 | 14 | 15 |
| Improving effect for skin complexion and gloss | Very effective | 15 | 0 | 0 | 0 | 0 |
| | Noticeably effective | 4 | 0 | 0 | 0 | 0 |
| | Slightly effective | 1 | 5 | 7 | 4 | 1 |
| | No effect | 0 | 15 | 13 | 16 | 19 |

As is clear from Table 4, the effect of the skin lotion of the present example containing the vitamin E orotate was remarkably high in moisturizing the dry and rough skins and improving the complexion and gloss of skins. Compared with this, the comparative lotions of Comparison Examples 5 through 8 merely had a slight or negligible effect in the moisturizng of skin and the improvement of the skin complexion and gloss.

EXAMPLE 3

Preparation of hair cream

An oil phase base containing vitamin E orotate was prepared by mixing the components of the composition as shown in Table 5 at a temperature of 80° C. Separately, an aqueous phase base was prepared by dissolving borax and propylene glycol in the composition as shown in Table 5, in distilled water at a temperature of 80° C. The aqueous phase base was added to the oil phase base while uniformly mixing them with stirring, and then, the mixture was gradually cooled to a temperature of about 30° C to prepare a hair cream of the present invention.

For comparative hear creams were prepared by the same method as mentioned above using, instead of the vitamin E orotate, vitamin E (Comparison Example 9), vitamin E acetate (Comparison Example 10), orotic acid (Comparison Example 11) and nothing (Comparison Example 12).

Table 5

| Base | Component | Example 3 | Comparison Example 9 | Comparison Example 10 | Comparison Example 11 | Comparison Example 12 |
|---|---|---|---|---|---|---|
| | | Composition (part by weight) | | | | |
| Oil phase | Bees wax | 5.0 | 5.0 | 5.0 | 5.0 | 5.0 |
| | Anhydrous lanolin | 4.0 | 4.0 | 4.0 | 4.0 | 4.0 |
| | Vaseline | 5.0 | 5.0 | 5.0 | 5.0 | 5.0 |
| | Liquid paraffin | 33.0 | 33.0 | 33.0 | 33.0 | 33.0 |
| | Glyceryl monostearate | 2.5 | 2.5 | 2.5 | 2.5 | 2.5 |
| | Addition product of cetyl alcohol with polyoxyethylene | 1.5 | 1.5 | 1.5 | 1.5 | 1.5 |
| | p-Hydroxybutyl benzoate | 0.1 | 0.1 | 0.1 | 0.1 | 0.1 |
| | Perfume | 0.5 | 0.5 | 0.5 | 0.5 | 0.5 |
| | Vitamin E orotate | 5.0 | — | — | — | — |
| | Vitamin E | — | 5.0 | — | — | — |
| | Vitamin E acetate | — | — | 5.0 | — | — |
| | Orotic acid | — | — | — | 5.0 | — |
| Aqueous phase | Borax | 0.3 | 0.3 | 0.3 | 0.3 | 0.3 |
| | Propylene glycol | 3.0 | 3.0 | 3.0 | 3.0 | 3.0 |

Table 5-continued

| Base | Component | Composition (part by weight) | | | | |
|------|-----------|---|---|---|---|---|
| | | Example | Comparison Example | | | |
| | | 3 | 9 | 10 | 11 | 12 |
| | distilled water | 40.1 | 40.1 | 40.1 | 40.1 | 45.1 |

EXAMPLE 4

Preparation of nutritious skin oil

In order to prepare a nutritious skin oil of the present invention containing vitamin E orotate, the components of the composition as shown in Table 11 were uniformly mixed.

Separately, four comparative skin oils were prepared in the same method as mentioned above using, instead of the vitamin E orotate, vitamin E (Comparison Example 13), vitamin E acetate (Comparison Example 14), orotic acid (Comparison Example 15) and nothing (Comparison Example 16).

Table 6

| Component | Composition (part by weight) | | | | |
|-----------|---|---|---|---|---|
| | Example | Comparison Example | | | |
| | 4 | 13 | 14 | 15 | 16 |
| Lanolin | 10 | 10 | 10 | 10 | 10 |
| Olive oil | 10 | 10 | 10 | 10 | 10 |
| Vaseline | 5 | 5 | 5 | 5 | 5 |
| Perfume | 0.5 | 0.5 | 0.5 | 0.5 | 0.5 |
| p-Hydroxybutyl benzoate | 0.1 | 0.1 | 0.1 | 0.1 | 0.1 |
| Vitamin E orotate | 10 | — | — | — | — |
| Vitamin E | — | 10 | — | — | — |
| Vitamin E acetate | — | — | 10 | — | — |
| Orotic acid | — | — | — | 10 | — |
| Liquid paraffin | 64.4 | 64.4 | 64.4 | 64.4 | 74.4 |

Throughout Examples 1 through 4, the vitamin E orotate used was orotic ester of dl-α-tocopherol. The same procedures as stated in Examples 1 through 4 were repeated using orotic esters of d-α-tocopherol, l-α-tocopherol, β-tocopherol, γ-tocopherol and δ-tocopherol instead of the orotic ester of dl-α-tocopherol. The cosmetics thus prepared has the same cosmetic effectiveness as shown in Examples 1 through 4.

What we claim is:

1. In a cosmetic compostion having an oil base, emulsion base or cream base for application to the human skin, the improvement which comprises employing in said cosmetic composition from 0.01% to 15.0% of vitamin E orotate based on the weight of the cosmetic composition.

2. A cosmetic composition according to claim 1 in which said vitamin E orotate is dissolved in an oil.

3. A cosmetic composition according to claim 1 in which said vitamin E orotate is dissolved in an alcohol solvent.

4. A cosmetic composition according to claim 1 wherein the amount of said vitamin E orotate is from 0.05% based on the weight of the cosmetic composition.

5. A cosmetic composition according to claim 1 wherein said vitamin E orotate is the orotic acid ester of a tocopherol selected from the group consisting of dl-α-tocopherol, d-α-tocopherol, l-α-tocopherol, β-tocopherol, γ-tocopherol and δ-tocopherol.

6. A cosmetic composition according to claim 1 wherein said cosmetic composition is selected from the group consisting of creams, lotions, hair cream and nutritious skin oil.

* * * * *

UNITED STATES PATENT AND TRADEMARK OFFICE
CERTIFICATE OF CORRECTION

PATENT NO. : 4,000,276
DATED : December 28, 1976
INVENTOR(S) : Kyotaro Hasunuma et al It is certified that error appears in the above-identified patent and that said Letters Patent are hereby corrected as shown below:

Col. 1, line 38 - change "or" to --of--.

Col. 3, line 67 - Table 2 - to "Improving effect for complexion and gloss" add --for skin--.

Col. 5, line 21 - between "suffered" and "dry" insert --from--.

Col. 8, line 29 - between "0.05%" and "based" insert --to 1.0%--.

Signed and Sealed this

Twelfth Day of April 1977

[SEAL]

Attest:

RUTH C. MASON
Attesting Officer

C. MARSHALL DANN
Commissioner of Patents and Trademarks